(12) United States Patent
Chen et al.

(10) Patent No.: US 11,409,344 B1
(45) Date of Patent: Aug. 9, 2022

(54) HEAD-MOUNTED HEAT DISSIPATION DEVICE

(71) Applicants: Guangzhou Tuowan Digital Technology Co., Ltd., Guangzhou (CN); Guangzhou Three Point One Design Co., Ltd., Guangzhou (CN)

(72) Inventors: Yanming Chen, Guangzhou (CN); Jiangtao Wu, Guangzhou (CN); Weicheng Zhuo, Guangzhou (CN); Canjie Lu, Guangzhou (CN)

(73) Assignees: Guangzhou Tuowan Digital Technology Co., Ltd., Guangzhou (CN); Guangzhou Three Point One Design Co., Ltd., Guangzhou (CN)

( * ) Notice: Subject to any disclaimer, the term of this patent is extended or adjusted under 35 U.S.C. 154(b) by 0 days.

(21) Appl. No.: 17/580,565

(22) Filed: Jan. 20, 2022

(30) Foreign Application Priority Data

Dec. 31, 2021 (CN) .......................... 202123455590.1

(51) Int. Cl.
*A42B 1/008* (2021.01)
*A42C 5/04* (2006.01)
*G06F 1/20* (2006.01)
*G06F 3/01* (2006.01)
*G02B 27/01* (2006.01)
(Continued)

(52) U.S. Cl.
CPC ........... *G06F 1/206* (2013.01); *A41D 13/005* (2013.01); *A41D 13/0025* (2013.01); *A41D 13/0053* (2013.01); *A42B 1/008* (2013.01); *A42B 3/286* (2013.01); *A42C 5/04* (2013.01); *A61F 7/007* (2013.01); *A61F 7/10* (2013.01); *F04D 25/084* (2013.01); *F04D 29/424* (2013.01); *F04D 29/444* (2013.01); *F24F 7/007* (2013.01); *G02B 27/0176* (2013.01); *G06F 1/163* (2013.01); *G06F 3/011* (2013.01); *F04D 25/0673* (2013.01); *F24F 2221/38* (2013.01); *G02B 2027/0161* (2013.01)

(58) Field of Classification Search
CPC ............ F04D 29/4226; F04D 29/4246; F04D 25/084; A41D 20/005; A41D 13/005; A41D 13/0025; A41D 13/0053; F24F 2221/38; F24F 7/007; A61F 2007/0009; A61F 2007/001; A61F 7/007; A61F 7/002; A61F 7/10; A42B 3/286; A24C 5/04
USPC ........................................ 415/101, 102, 103
See application file for complete search history.

(56) References Cited

U.S. PATENT DOCUMENTS

| | | | | |
|---|---|---|---|---|
| 4,680,815 A | * | 7/1987 | Hirsch | ............... A42C 5/04 2/171.3 |
| 5,561,862 A | * | 10/1996 | Flores, Sr. | ............ A42B 3/286 2/422 |

(Continued)

*Primary Examiner* — Christopher Verdier
*Assistant Examiner* — Andrew J Marien
(74) *Attorney, Agent, or Firm* — Georgi Korobanov

(57) ABSTRACT

A head-mounted heat dissipation device includes a fan assembly and a wearing assembly. The wearing assembly is connected to the fan assembly to fix the fan assembly onto a head of a user. The fan assembly includes a casing and fans arranged in the casing. Air inlets and air outlets are defined in the casing. The air outlets are located on an inner side of the bottom surface of the casing, so that the air from the air outlets can be blown to the user's face. In addition, air guide strips are arranged side by side on a side of the air outlet within the casing for concealing the operation of the fans.

9 Claims, 2 Drawing Sheets

(51) Int. Cl.
*G06F 1/16* (2006.01)
*F04D 25/08* (2006.01)
*F04D 29/44* (2006.01)
*F04D 29/42* (2006.01)
*A42B 3/28* (2006.01)
*A61F 7/00* (2006.01)
*A41D 13/002* (2006.01)
*A41D 13/005* (2006.01)
*A61F 7/10* (2006.01)
*F24F 7/007* (2006.01)
*F04D 25/06* (2006.01)

(56) References Cited

U.S. PATENT DOCUMENTS

| | | | | |
|---|---|---|---|---|
| 5,754,983 A | * | 5/1998 | Landers | A42B 1/201 2/10 |
| 6,032,291 A | * | 3/2000 | Asenguah | A42B 1/008 2/209.13 |
| 6,081,929 A | * | 7/2000 | Rothrock | A42B 3/286 2/424 |
| 6,122,773 A | * | 9/2000 | Katz | A42B 3/286 2/422 |
| 8,480,365 B2 | * | 7/2013 | Ochoa | F04D 29/601 416/63 |
| 9,486,026 B1 | * | 11/2016 | Cook, Sr. | F04D 25/084 |
| 10,128,034 B2 | | 11/2018 | Lu et al. | |
| 10,278,442 B2 | * | 5/2019 | Wang | F04D 29/282 |
| 10,579,111 B1 | | 3/2020 | Jenkins et al. | |
| 11,131,310 B1 | * | 9/2021 | Emery | A42B 1/008 |
| 2009/0031475 A1 | * | 2/2009 | Ochoa | A42B 1/244 2/209.13 |
| 2010/0017941 A1 | * | 1/2010 | Taylor | A42B 1/008 2/209.13 |
| 2017/0332721 A1 | * | 11/2017 | Otey | A42B 3/227 |
| 2018/0007993 A1 | * | 1/2018 | Moreno | A42B 3/125 |

* cited by examiner

HEAD-MOUNTED HEAT DISSIPATION DEVICE

CROSS-REFERENCE TO RELATED APPLICATIONS

This application claims the benefit and priority of Chinese patent application No. 202123455590.1, filed on Dec. 31, 2021, disclosure of which is hereby incorporated by reference in its entirety.

TECHNICAL FIELD

The utility model relates to the technical field of heat dissipation devices, in particular to a head-mounted heat dissipation device.

BACKGROUND

Generally speaking, the function of a hat is to protect the user from sunburn. Taking a peaked cap as an example, it includes a main body and a visor, where the main body covers the head of the user and serves a sun protection and a fixation function to be fixed to the top of the head. The visor at the front edge has the effect of shading the face from sunlight. However, in a hot environment, since the main body of the hat is closely attached to the user's head, it is easy to produce a stuffy feeling, and even make the head sweat thus soaking the hair. In this way, although wearing a hat can achieve the purpose of shading and sun protection, it is easy to make users feel extremely uncomfortable. In order to meet the requirements of users, a fan and other heat dissipation devices are installed on the hat to solve the problem.

In order to meet the requirements of air volume and reduce the weight burden of the product itself, the current head-mounted heat sinks on the market adopt an open fan design. In the process of use, the open fan design is likely to cause the user's hair to be entangled in the fan blades, causing danger and affecting the safety of the product.

SUMMARY

In order to overcome the shortcomings of the related art, the technical problem to be solved by the present utility model is to propose a head-mounted heat dissipation device. The overall structure of the device is optimized to solve the problem of the use of open fan in the head-mounted heat sink product.

To achieve this purpose, the utility model adopts the following technical solutions.

The utility model provides a head-mounted heat dissipation device, which includes a fan assembly and a wearing assembly. The wearing assembly is connected to the fan assembly and configured to fix the fan assembly onto a head of a user. The fan assembly includes a casing and fans arranged in the casing. Air inlets and air outlets are defined in the casing. The air outlets are located on an inner side of the bottom surface of the casing, so that the air from the air outlets can be blown to the user's face. In addition, air guide strips are arranged side by side on a side of the air outlet within the casing for concealing the operation of the fans, and the casing includes an upper casing and a lower casing, wherein the upper casing is buckled on the lower casing to form an internal space, wherein the fans are centrifugal fans, which are disposed inside the casing. The upper casing includes first air inlets, which are disposed on one end of the shaft of the centrifugal fan. The lower casing includes second air inlets, which are disposed on the other end of the shaft of the centrifugal type.

According to an illustrative technical solution of the present utility model, the casing is configured as a flat shape.

According to an illustrative technical solution of the present utility model, a grille is arranged at the air outlets, and the air guide strips are attached to the grille.

According to an illustrative technical solution of the present utility model, the lower casing is provided with air guide grooves, the centrifugal fans are located on a first side of the air guide grooves, the side of one end of the shaft of the centrifugal fan is connected with a fixed rod of the air guide groove, and the air outlets comprise a first air outlet and a second air outlet and are arranged on a second side of the air guide groove.

According to an illustrative technical solution of the present utility model, the centrifugal fans comprise a first centrifugal fan and a second centrifugal fan. The air guiding grooves include a first air guiding groove and a second air guiding groove, which are respectively located on the left and right sides of the lower casing. The first centrifugal fan is disposed on an inner side of the first air guide groove, and the first air outlet is disposed on a second side of the first air guide groove. The second centrifugal fan is located on an inner side of the second air guide groove, and the second air outlet is arranged on a second side of the second air guide groove.

According to an illustrative technical solution of the present utility model, the first air guide groove and the second air guide groove are of a volute structure, the centrifugal fans are located inside the volute, and the air outlets are located at the volute mouth.

According to an illustrative technical solution of the present utility model, a battery is included and is located inside the casing, the battery and the fans are electrically connected, and the battery is arranged adjacent to the forehead.

According to an illustrative technical solution of the present utility model, the wearing assembly includes a headband for adjusting the tightness.

The beneficial effects of the utility model are as follows:

The utility model proposes a head-mounted heat dissipation device. The design provides an air outlet on the inner side of the bottom surface of the casing and replaces the ordinary shielding structure with air guide strips. The direction pointed by the row of the air guide strips is consistent with the direction in which the fan blows, so that it can not only guide the flow of the wind, but also prevent the danger of foreign objects touching the fan blades, and the user cannot see the rotating fan blades due to the shielding of the air guide strips, making it more comfortable to use.

BRIEF DESCRIPTION OF DRAWINGS

For a clearer understanding of the technical solutions that are used in the embodiments according to the present disclosure or that are used in the related art, hereinafter the drawings that are required for the description of the embodiments disclosed herein or the related art will be briefly introduced. Apparently, the drawings in the following description merely represent some embodiments of the present disclosure, and for those having ordinary skill in the art, other drawings may also be obtained based on these drawings without investing creative efforts.

Figure 1:
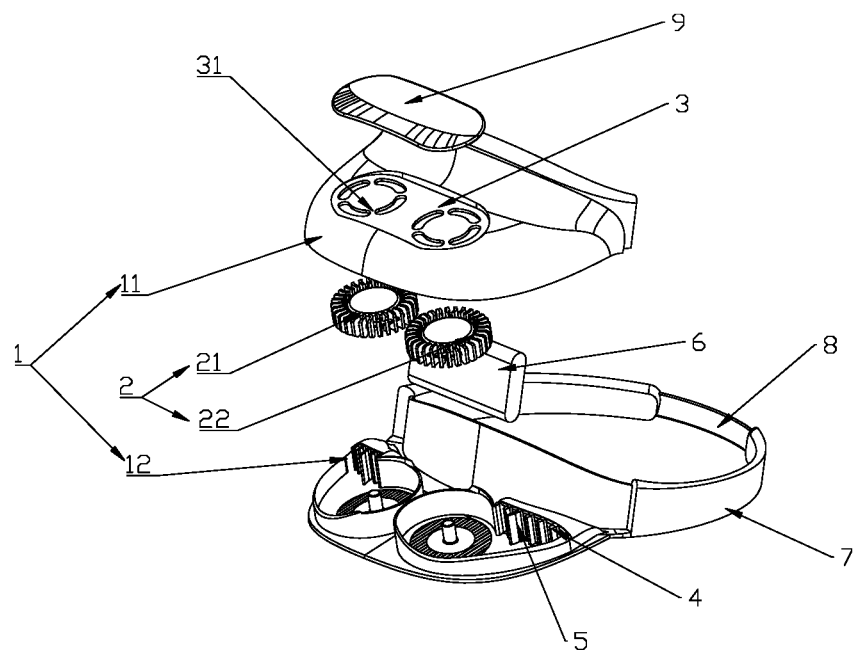
FIG. 1 is an exploded view of a head-mounted heat dissipation device of the utility model.

In the drawings:
1, casing; 11, upper casing; 12, lower casing; 121, first air guide groove; 122, second air guide groove; 2. centrifugal fan; 21, first centrifugal fan; 22, second centrifugal fan; 3, air inlet; 31, first air inlet; 32, second air inlet; 4. air outlet; 41, first air outlet; 42, second air outlet; 5. air guide strip; 6, battery; 7, headband; 8, elastic band; 9, air outlet cover.

DETAILED DESCRIPTION

The technical solution of the present utility model will be further explained below with reference to the drawings and specific implementations.

Figure 2:
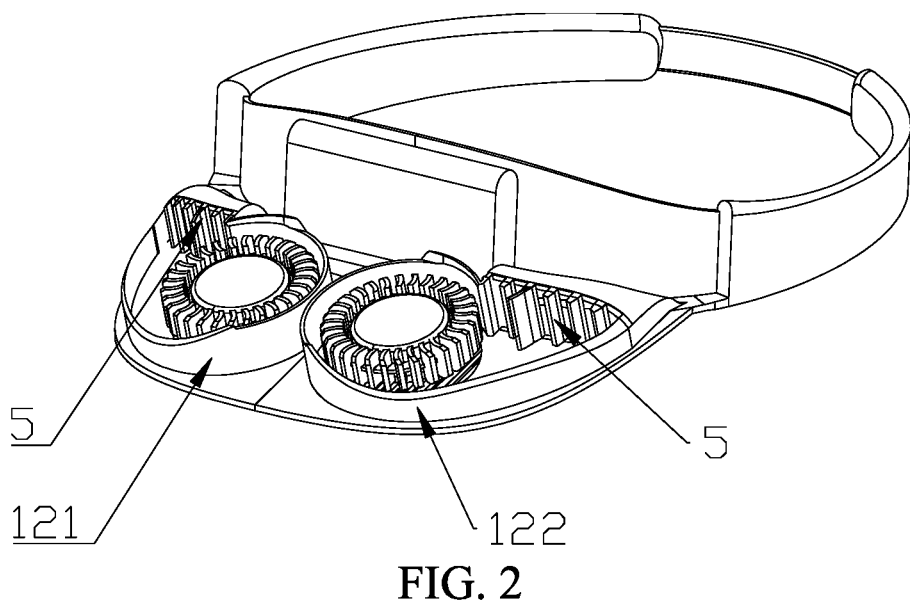
FIG. 2 is a partial structure diagram of a head-mounted heat dissipation device of the utility model.
Figure 3:
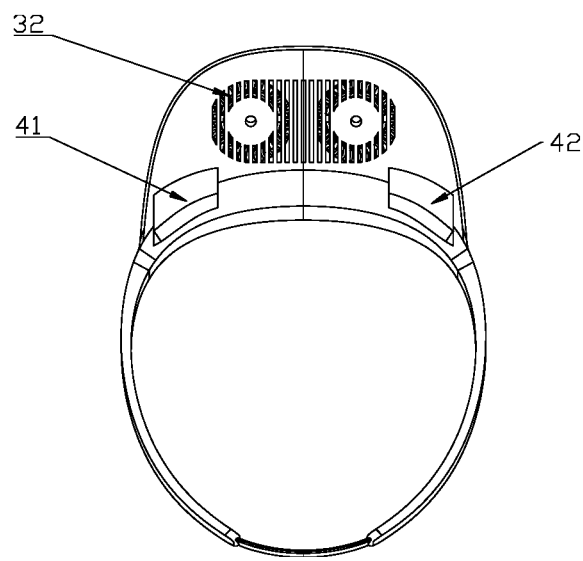
FIG. 3 is a structural diagram of a head-mounted heat dissipation device of the present utility model.

As shown in FIGS. 1-3, this embodiment provides a head-mounted heat dissipation device, which includes a fan assembly and a wearing assembly. The wearing assembly is connected to the fan assembly to fix the fan assembly onto the head. The fan assembly includes a casing 1 and fans arranged in the casing 1. Air inlets 3 and air outlet 4 are defined in the casing 1. The air outlets 4 are located on an inner side of the bottom surface of the casing 1, so that the air from the air outlets 4 can be blown to the user's face. In addition, air guide strips 5 are arranged side by side on a side of the air outlets 4 within the casing 1 for concealing the operation of the fan. This design provides an air outlet on the inner side of the bottom surface of the casing and replaces the ordinary shielding structure with air guide strips. The direction pointed by the row of the air guide strips is consistent with the direction in which the fan blows, so that it can not only guide the flow of the wind, but also prevent the danger of foreign objects touching the fan blades, and the user cannot see the rotating fan blades due to the shielding of the air guide strips, making it more comfortable to use.

In order to facilitate the flow of the wind blown by the fan, preferably, the housing 1 is provided in a flat shape.

In order to prevent foreign objects from touching the running fan blades, grilles are specifically set at the air inlets 3 and the air outlets 4, wherein the air guide strips 5 are attached to the grille of the air outlets 4.

To facilitate assembly, specifically, the casing 1 includes an upper casing 11 and a lower casing 12, and the upper casing 11 is buckled on the lower casing 12 to form an internal space.

In order to make reasonable use of the flat space, specifically, the fans are centrifugal fans 2, which are disposed inside the casing 1. The upper casing 11 includes first air inlets 31, which are disposed on one end of the shaft of the centrifugal fan 2. The lower casing 12 includes second air inlets 32, which are disposed on the other end of the shaft of the centrifugal fan 2. The centrifugal fan lies flat inside the casing, and the airflow enters the blade space from the fan axially, and then rotates with the impeller under the drive of the impeller. On the other hand, it increases energy under the action of inertia and leaves the impeller along the radius. This design changes the air duct flow direction of some axial fans, making the structure more reasonable, and it can better conceal the rotating fan blades and blow out stronger wind at the same time.

Further, the lower casing 12 is provided with air guide grooves, the centrifugal fans 2 are located on a first side of the air guide grooves, the side of one end of the shaft of the centrifugal fan 2 is connected with a fixed rod of the air guide groove, and the air outlets 4 are arranged on a second side of the air guide groove. Through the arrangement of the air guide groove, the wind force of the centrifugal fan on the first side leaving the impeller is concentrated and flows out to the air outlet on the second side. Preferably, the shape of the air guide groove is a volute structure, the centrifugal fans 2 are located inside the volute, and the air outlets 4 are located at the volute opening. This structure can effectively gather and blow air.

In order to further increase the wind power, specifically, the centrifugal fans 2 include a first centrifugal fan 21 and a second centrifugal fan 22. The air guiding grooves include a first air guiding groove 121 and a second air guiding groove 122, which are respectively located on the left and right sides of the lower casing 12. The first centrifugal fan 21 is disposed on an inner side of the first air guide groove 121, and the first air outlet 41 is disposed on a second side of the first air guide groove 121. The second centrifugal fan 22 is located on an inner side of the second air guide groove 122, and the second air outlet 42 is arranged on a second side of the second air guide groove 122. Two centrifugal fans are located in the middle of the inside of the hat to reduce the burden on the user. The two air outlets emit wind from both sides of the user, covering a wide range of heat dissipation area, and the wind directions are even. In this embodiment, in order to further increase the wind power, a double air inlet design is adopted, and a first air inlet 31 and a second air inlet 32 are respectively provided on the upper casing and the lower casing. Furthermore, the upper casing is provided with a fan cover 9 and a gap is left between the first air inlet 31 and the fan cover 9 to facilitate the introduction of outside wind, and at the same time prevent hair or other foreign objects from entering and contacting the fan blades.

Since the battery generates heat during use, in order to reduce the heat being sent out along the air duct, preferably, the following solution is provided in which the battery 6 is included and is located inside the casing 1, and the battery 6 is electrically connected to the fan, and the battery 6 is arranged adjacent to the forehead. This design is also conducive to maintaining the balance and stability of wearing.

In order to adjust the tightness of the headband so that the product is suitable for people with different head sizes and has a comfortable wearing feeling, the wearing assembly includes a headband 7 for adjusting the tightness, and the headband 7 is provided with an elastic band 8.

The present utility model is described by means of illustrative embodiments. Those skilled in the art know that various changes or equivalent substitutions can be made to these features and embodiments without departing from the spirit and scope of the present utility model. The present utility model is not limited by the specific embodiments disclosed herein, and other embodiments falling into the scope defined in and by the claims of the present utility model shall all fall in the scope of protection of the present utility model.

What is claimed is:

1. A head-mounted heat dissipation device, comprising a fan assembly and a wearing assembly, wherein the wearing assembly is connected to the fan assembly and configured to fix the fan assembly to a head of a user, wherein the fan assembly comprises a casing and fans arranged in the casing, wherein the casing comprises air inlets and air outlets, wherein the air outlets are disposed on an inner side of a bottom surface of the casing, to facilitate air from the air outlets to be blown toward the user, and wherein air guide strips are arranged side by side on a side of the air outlets within the casing and are used for concealing operation of the fans, wherein the casing comprises an upper casing and a lower casing, and wherein the upper casing is buckled on the lower casing to form an internal space, and the fans are centrifugal fans, which are disposed inside the casing, wherein the upper casing comprises first air inlets located at a side at one end of a shaft of the centrifugal fan, wherein the lower casing comprises second air inlets located at a side at another end of the shaft of the centrifugal fan.

2. The head-mounted heat dissipation device as recited in claim 1, wherein the casing is of a flat shape.

3. The head-mounted heat dissipation device as recited in claim 1, wherein a grille is arranged at each air outlet, and the air guide strips are attached to the grilles.

4. The head-mounted heat dissipation device as recited in claim 1, wherein the lower casing comprises air guide grooves, wherein the centrifugal fans are disposed on the first side of the air guide grooves, wherein one end of the shaft of the centrifugal fan is connected with a fixing rod of the air guide groove, and the air outlets comprise a first air outlet and a second air outlet and are arranged on the second side of the air guide groove.

5. The head-mounted heat dissipation device as recited in claim 4, wherein the centrifugal fans comprises a first centrifugal fan and a second centrifugal fan; the air guide grooves comprises a first air guide groove and a second air guide groove, which are respectively disposed on a left and a right side of the lower casing, the first centrifugal fan is disposed on an inner side of the first air guide groove, the first air outlet is arranged on a second side of the first air guide groove, and wherein the second centrifugal fan is disposed on an inner side of the second air guide groove, and the second air outlet is arranged on a second side of the second air guide groove.

6. The head-mounted heat dissipation device as recited in claim 5, wherein the first air guide groove and second air guide groove are of a volute structure, the centrifugal fans are disposed inside the volute, and the air outlets are disposed at a mouth of the volute.

7. The head-mounted heat dissipation device as recited in claim 5, wherein the first air guide groove and second air guide groove are of a volute structure, the centrifugal fans are disposed inside the volute, and the air outlets are disposed at a mouth of the volute.

8. The head-mounted heat dissipation device as recited in claim 1, further comprising a battery disposed inside the casing and electrically connected to the fans.

9. The head-mounted heat dissipation device as recited in claim 1, wherein the wearing assembly comprises a headband configured for adjusting tightness.

* * * * *